(12) United States Patent
Roe

(10) Patent No.: US 8,118,824 B2
(45) Date of Patent: Feb. 21, 2012

(54) MAGNETIC POWERED LANCING DRIVE

(75) Inventor: Steven N. Roe, San Mateo, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 452 days.

(21) Appl. No.: 12/211,408

(22) Filed: Sep. 16, 2008

(65) Prior Publication Data

US 2010/0069943 A1   Mar. 18, 2010

(51) Int. Cl.
*A61B 17/32* (2006.01)
(52) U.S. Cl. ....................................... 606/181
(58) Field of Classification Search ............... 606/181, 606/182, 183, 189; 600/583
See application file for complete search history.

(56) References Cited

U.S. PATENT DOCUMENTS

| | | | |
|---|---|---|---|
| 3,601,372 A * | 8/1971 | Harmes | 366/219 |
| 3,840,088 A | 10/1974 | Marumo et al. | |
| 4,924,879 A * | 5/1990 | O'Brien | 600/583 |
| 5,938,679 A | 8/1999 | Freeman et al. | |
| 6,080,172 A | 6/2000 | Fujiware | |
| 6,231,531 B1 | 5/2001 | Lum et al. | |
| 6,265,957 B1 | 7/2001 | Baginski et al. | |
| 6,306,152 B1 * | 10/2001 | Verdonk et al. | 606/182 |
| 6,364,889 B1 | 4/2002 | Kheiri et al. | |
| 6,646,529 B1 | 11/2003 | Kahnert | |
| 2003/0212424 A1 | 11/2003 | Briggs et al. | |
| 2004/0049219 A1 | 3/2004 | Briggs et al. | |
| 2004/0155743 A1 | 8/2004 | Sako | |
| 2007/0038149 A1 | 2/2007 | Calasso et al. | |
| 2007/0167874 A1 | 7/2007 | Freeman et al. | |
| 2008/0188883 A1 | 8/2008 | Deck et al. | |

(Continued)

FOREIGN PATENT DOCUMENTS

EP   1 063 666 A2   12/2000

(Continued)

OTHER PUBLICATIONS

International Application No. PCT/EP2009/006588 International Search Report/Written Opinion mailed Jun. 15, 2010.

(Continued)

*Primary Examiner* — Elizabeth Houston
*Assistant Examiner* — Sarah Simpson
(74) *Attorney, Agent, or Firm* — Woodard, Emhardt, Moriarty, McNett & Henry LLP

(57) ABSTRACT

A self-powered lancing drive system and lancing technique uses permanent magnets to initially store the potential energy that is converted to kinetic energy for extending a lancet during lancing. This self-powered lancing drive system is a pure permanent magnet drive that is highly reliable under numerous operating conditions. Permanent magnets can produce stronger magnetic fields at smaller sizes as compared to electromagnets. In one form, the lancing system has a drive permanent magnet that is kept fixed or stationary while the lancet magnet travels along the firing path. With the drive magnet being stationary, the lancet experiences fewer fluctuations in the magnetic field. The lancet vibrates less and is driven straighter into the tissue. In another form, a retraction magnet is positioned at the end of the firing path of the lancet, near the tissue, to enhance retraction of the lancet. In another form, a mechanical structure keeps the magnets in close proximity so that the strength of the magnetic propulsion force is maintained. The mechanical structure in one example is a crank mechanism that confines magnet movement to a circular path. The crank mechanism provides a smooth lancing profile as well as facilitates adjustments to the lancing profile.

14 Claims, 7 Drawing Sheets

U.S. PATENT DOCUMENTS

| | | | |
|---|---|---|---|
| 2008/0269639 A1* | 10/2008 | Korner et al. | 600/583 |
| 2009/0030441 A1* | 1/2009 | Kudrna et al. | 606/181 |
| 2009/0043324 A1* | 2/2009 | Paschal | 606/181 |
| 2009/0306695 A1* | 12/2009 | Brenneman | 606/181 |

FOREIGN PATENT DOCUMENTS

| | | |
|---|---|---|
| JP | H02-095352 | 4/1990 |
| JP | H02-095352 A | 4/1990 |
| JP | 2003-339680 | 12/2003 |
| JP | 2003-339680 A | 12/2003 |
| WO | WO 02/100460 A2 | 12/2002 |
| WO | WO 2006/116441 A1 | 11/2006 |

OTHER PUBLICATIONS

International Patent Application PCT/EP2009/006588 Extended Search Report mailed Mar. 22, 2011.

* cited by examiner

MAGNETIC POWERED LANCING DRIVE

BACKGROUND

Most current lancing devices use some form of a spring-type mechanism to drive the lancet into the skin. These mechanical spring-type lancing devices have several drawbacks, such as inconsistent lancing profiles, spring vibration, cocking problems, etc., that can increase the pain and frustration associated with lancing. Such spring-type lancing mechanisms have also proven to be noisy which in turn can increase apprehension of the user. It has been previously suggested that electromagnets can be used to drive lancets in order to form incisions in the skin. While the use of electromagnets can provide relatively smooth and controllable lancing profiles, which in turn can reduce pain, these types of systems are bulky and expensive to both produce and use. Meters are typically portable and need a portable power source. For example, electromagnetic-type systems require external sources of power, such as batteries, that increase their size, weight, and expense. Batteries also tend to drain at the most inappropriate times, which can be problematic for testing in third world developing countries as well as in situations where batteries are not readily available like during camping.

Hybrid systems have been proposed that incorporate components from both the spring-type and magnetic-type lancing devices. For example, WO 2006/116441 A1 to Bayer Healthcare LLC describes a lancing device that includes a moveable element in the form of a disk (or linear slide) that has a series of magnets with alternating polarities for actuating a plunger mechanism that has a lancet. A torsion spring (or the user) rotates the disk that in turn causes the lancet to extend and retract. However, these hybrid systems are still subject to many of the problems associated with the individual spring-type and magnetic-type lancing devices.

Thus, needs remain for further contributions in this area of technology.

SUMMARY

The inventor has made a number of significant discoveries about the previously described lancing systems. It can be observed in the above-mentioned hybrid spring-magnet lancing device that the magnets were merely used to transmit the kinetic energy of the disk to the plunger mechanism. As such, the hybrid spring-magnet lancing device was still reliant on mechanical springs to provide the requisite energy for lancing. The spring in such a hybrid system is still typically noisy such that the user can become scared or apprehensive when the lancet is fired. Of particular concern, springs in such hybrid systems can deform or develop memory as they age, and as a result, the force provided by the springs can reduce or vary over time, which in turn can lead to inconsistent lancing profile speeds. Temperature fluctuations can also adversely affect properties of the spring which in turn can change the lancing profile speeds. These slower and/or variable lancing speeds can create quite painful experiences for the user.

In addition, it has been discovered that the magnetic fields generated by these hybrid spring-magnet lancing devices fluctuate and are unevenly applied such that the lancet can skew and/or vibrate during the lancing procedure. For example, one side of the lancet magnet can experience a greater (or lesser) attractive or repelling force as the magnets on the disk move relative to the lancet. This in turn causes the lancet to skew and not penetrate the tissue at a right angle, thereby increasing penetration depth variation as well as the associated pain. The skewing can also lead to vibration of the lancet which can increase pain as well.

It was found that another issue with the hybrid design is that the magnet for retracting the lancet is located far away from the lancet carrier when the lancet is at its farthest extended position. This construction necessitates the use of more powerful and expensive magnets that can interfere with the magnets that are used to fire the lancet. Even minor fluctuations in the magnetic field are magnified by the greater distance, which in turn can create penetration depth variability.

It has been also observed that the ballistic design of the hybrid and electromagnetic drive systems are inflexible as to the lancing profiles they provide. In other words, there is very little ability to adjust the speed to the lancet during the extension and retraction strokes.

Considering lancets are usually disposable in nature, lancets are manufactured to be small and consequently light. As a result, the decreased mass of the lancet provides less momentum when the lancet is fired. The lower momentum adversely affects the ability of the lancet to puncture tissue.

The lancing systems and methods described herein alleviate these issues as well as others by using permanent magnets to initially store the potential energy that is converted to kinetic energy for extending the lancet during lancing. This self-powered lancing drive system eliminates the need for problematic springs and batteries. In other words, the lancing system is a pure permanent magnet drive is highly reliable under numerous operating conditions. Permanent magnets can produce stronger magnetic fields at smaller sizes as compared to electromagnets.

In another aspect, the lancing system has a drive permanent magnet that is kept fixed or stationary while the lancet magnet travels along the firing path. To put it another way, the permanent drive magnet that is at least stationary before the lancet punctures the skin as well as when the lancet is beneath the tissue. With the drive magnet being fixed, the lancet experiences fewer fluctuations in the magnetic field. Consequently, the lancet vibrates less and is driven straighter into the tissue. This also reduces vibrations when the lancet is within the skin and being withdrawn during the retraction stroke.

In the system, the magnet used to retract the lancet remains relatively close to the magnet attached to the lancet so that the retraction force applied is strong, thereby leading to more consistent penetration depths. In one example, the retraction magnet is positioned at the end of the firing path of the lancet, near the skin or other tissue. In another example, a mechanical structure keeps the magnets in close proximity. The mechanical structure in one form is a crank member that confines the magnets to a circular path. The crank mechanism provides a smooth lancing profile as well as facilitates adjustments to the lancing profile. These mechanical structures and/or linkages can also enhance the momentum for the relatively light disposable lancets.

The system described herein also facilitates for self-powered systems contactless cocking in which the user does not have to move the lancet or plunger to perform cocking, but instead the user simply changes the polarity between the magnets in order to create the potential for firing the lancet. The contactless cocking reduces the risk of wear and tear on the plunger mechanism as well as prevents any jamming of the plunger when the user manually cocks the plunger. It also avoids the user sticking their fingers inside the lancing mechanism, thereby reducing a potential contamination source. Between tests the contactless cocking mechanism is designed to secure the lancet carrier so as to reduce a source of injury. The carrier is secured at a fixed location so as to avoid any bottoming out issues when the lancet is loaded.

The permanent magnet lancing system described herein uses permanent magnets to both extend and retract the lancet during lancing. In other variations, combinations of permanent magnets and electromagnets can be used as well. It uses both the attracting and repelling forces of high powered permanent magnets, such as neodymium-Iron-Boron over the traditional use of metal springs to drive the firing mechanism. By using magnetic power, different combinations of motor drives are possible and can be used to provide the speed and power to lance the finger for producing a small blood sample. In still yet other variations, other forces with attracting and repelling properties, such as electrostatic forces, can be used to drive the lancet.

In one embodiment, three magnets are used for firing and retracting the lancet. A first fixed drive or firing magnet provides the repelling, ballistic force to fire a lancet mounted to a second movable magnet, and a third fixed retraction magnet is used to provide the repelling force that retracts the lancet. In particular, the second movable magnet is mounted on a lancet carrier that moves in a generally linear fashion. Before firing, the second, movable magnet is clamped against the first magnet. Once the clamp is released, the repelling force between the magnets causes the lancet to be fired into the skin. The third magnet causes the lancet to decelerate, gently stop and reverse direction, thereby retracting the lancet.

In another embodiment, a piston and crank arrangement is used along with three magnets to fire and retract the lancet. A fixed magnet is attached to the base of the drive mechanism, and two free magnets are attached to the half-circle shaped crank. Before firing the lancet, the common polarity sides of the fixed magnet and one of the free magnets are clamped together and held in place with a latch or trigger. Once the latch is released, the repelling force of the magnets causes the crank to rotate, which in turn fires the lancet. Once the crank passes the halfway point, the other free magnet on the crank is attracted to the fixed magnet, which causes the lancet to retract.

Further forms, objects, features, aspects, benefits, advantages, and embodiments of the present invention will become apparent from a detailed description and drawings provided herewith.

DESCRIPTION OF THE SELECTED EMBODIMENTS

Figure 1:
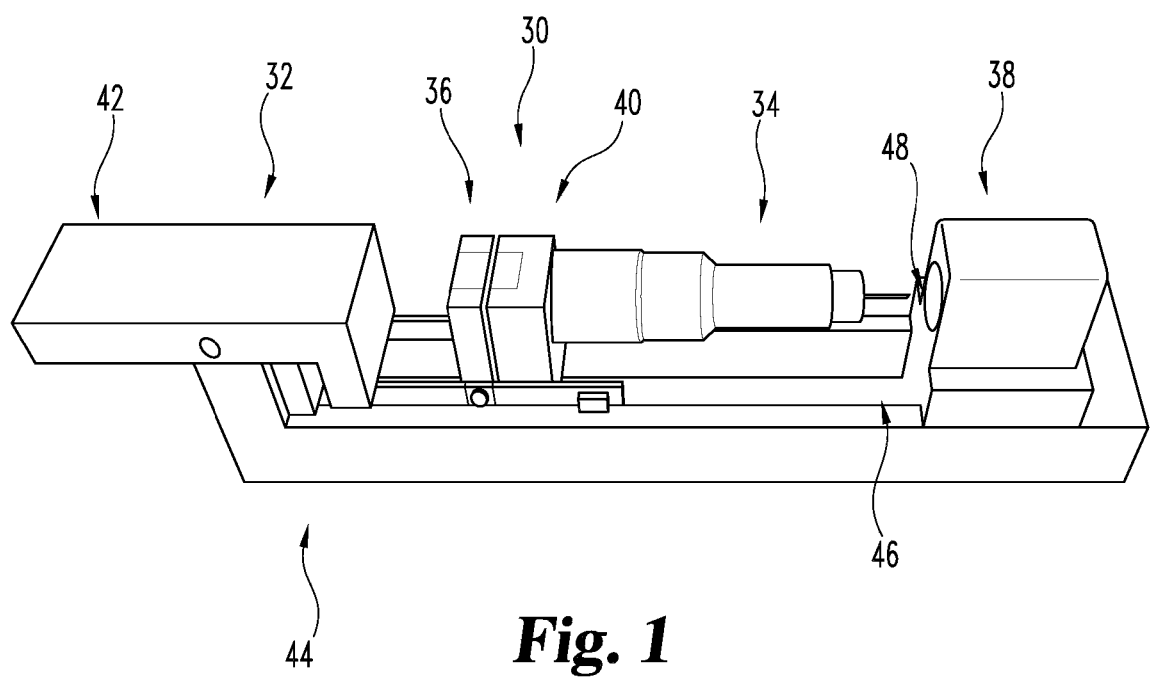
FIG. 1 is a perspective view of a lancing device according to one embodiment.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

FIG. 1 shows a perspective view of a lancing system or device 30 according to one embodiment. It should be noted that other components of the lancing device 30 in FIG. 1, such as the housing, have been removed so that the structure and function of the components in the lancing device 30 can be clearly seen. Looking at FIG. 1, the lancing device 30 has a fixed drive or firing magnet 32 that provides the repelling, ballistic force to fire a lancet 34 coupled to a movable lancet carrier magnet 36. A retraction magnet 38 is used to provide the repelling force that retracts the lancet 34. The position of the retraction magnet 38 can be changed to adjust the penetration depth of the lancet 34. As can be seen, the movable lancet carrier magnet 36 is mounted on a lancet carrier 40 that moves in a generally linear fashion. Before firing, a trigger 42 in the form of a latch holds the lancet carrier magnet 36 against or in close proximity to the fixed drive magnet 32. Once the trigger 42 is released, the repelling force between the magnets causes the lancet 34 to be fired into the skin or other tissue. The retraction magnet 38 causes the lancet 34 to decelerate, gently stop and reverse direction, thereby retracting the lancet 34 from the tissue.

In the illustrated embodiment, the drive 32, lancet carrier 36, and retraction 38 magnets are permanent magnets. Permanent magnets provide greater magnetic force with a more compact design as compared to electromagnets. Using permanent magnets to create the potential energy for firing the lancet 34 also makes the lancing device 30 highly reliable under various operating conditions. The lancing device 30 in FIG. 1 is completely self-powered, and the lancing device 30 does not need other power sources, such as problematic springs or batteries, to lance tissue. Moreover, with the drive magnet 32 being generally fixed in position, the lancet carrier 40 experiences less magnetic field fluctuations, and as a result, the lancet 34 is fired straighter and truer with minimal lancet vibrations.

In the previously mentioned hybrid spring-magnet lancing device, the magnet for retracting the lancet was located away from the lancet when in the extended state. With such an arrangement, the retraction force became weaker as the lancet traveled farther away from the retraction magnet when fired. The weaker retraction force resulted in penetration depths that could not be tightly controlled. In contrast, looking at FIG. 1, the retraction magnet 38 is located near the end of the firing stroke such that as the lancet 34 travels closer to the retraction magnet 38, the repulsive force becomes stronger. This allows the lancet 34 to decelerate and retract in a smooth fashion. Of particular interest, the penetration depth of the lancet 34 can be tightly controlled with this arrangement.

The specific structural aspects of the lancing device 30 will now be described with reference to FIG. 1. In FIG. 1, the housing for the lancing device has been removed so that the various components of the lancing device 30 can be easily viewed, and it should be recognized that the lancing device 30 can include a housing as well as other components. As shown, the drive magnet 32 is secured to one end of a support structure 44, and the retraction magnet 38 is secured to the opposite end of the support structure 44. At the same end as the drive magnet 32, the trigger 42 is pivotally secured to the support structure 44 so that the trigger can engage and release the lancet carrier 40. The support structure 44 has a guide channel 46 in which the lancet carrier 40 is slidably received for guiding the carrier during both firing and retraction movements. The carrier 40 and/or the support structure 44 can further include structures or other means for reducing friction between the carrier and the guide channel 46, like wheels, rollers, magnetic bearings, friction reducing materials (e.g., TEFLON®), and the like.

The lancet 34 is detachably secured to the carrier 40 through a friction fit connection so that the lancet 34 can be replaced after each use, if so desired. The lancet carrier magnet 36 is positioned on the carrier 40 to face the drive magnet 32. The sides of the drive 32 and lancet carrier 36 magnets facing each other have like poles so that they repel. For example, in one embodiment, the drive magnet 32 and the lancet carrier magnet 36 have their respective North poles facing one another, and in another embodiment, the South poles face one another.

In a similar fashion, the sides of the lancet carrier 36 and retraction 38 magnets facing each other have like poles so that they repel. For example, in one embodiment, the lancet carrier magnet 36 and the retraction magnet 38 have their respective North poles facing one another, and in another embodiment, the South poles face one another. As noted before, this configuration allows the lancet 34 to decelerate, gently stop and reverse direction in order to retract the lancet 34 from the tissue. The retraction magnet 38 in the illustrated embodiment includes a lancet opening 48 through which the lancet 34 extends in order to pierce the tissue.

During use, the user cocks the lancing device 30 by pushing the lancet carrier 40 against or in close proximity to the drive magnet 32, and the lancet 34 can be loaded on the lancet carrier 40 before or after the lancing device 30 is cocked. The trigger 42 holds the lancet carrier 40 in place. The user typically places the lancing device 30 on the target tissue after the lancing device 30 is cocked, but this placement on tissue can occur before the lancing device 30 is cocked. To fire the lancet 34, the user actuates the trigger 42, which in turn causes the trigger 42 to release the lancet carrier 40. The repulsive magnetic force between the drive 32 and lancet carrier 36 magnets causes the lancet 34 to fire. In other words, the potential energy between the drive 32 and lancet carrier 36 magnets is converted to the kinetic energy that fires the lancet 34. Subsequently, the lancet 34 pierces the tissue, and the repulsive magnetic force between the lancet carrier 36 and retraction 38 magnets causes the lancet 34 to retract out of the newly cut incision. After the lancet 34 is retracted, the user can discard the now used lancet 34 and replace it with a new one. The lancing device 30 is then ready to be cocked and fired in the same fashion described above.

Figure 2:
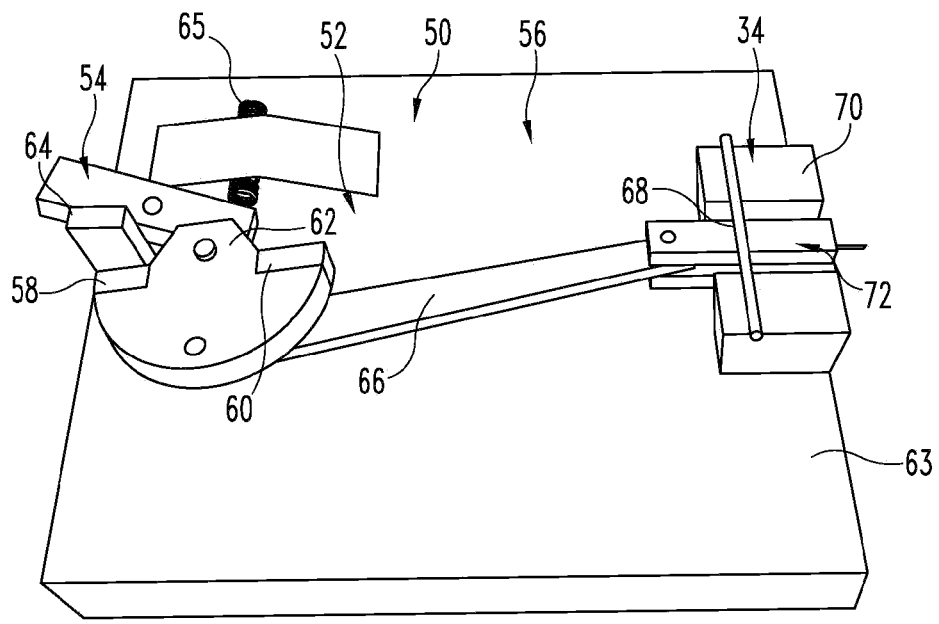
FIG. 2 is a first perspective view of a crank-type lancing mechanism according to another embodiment.
Figure 3:
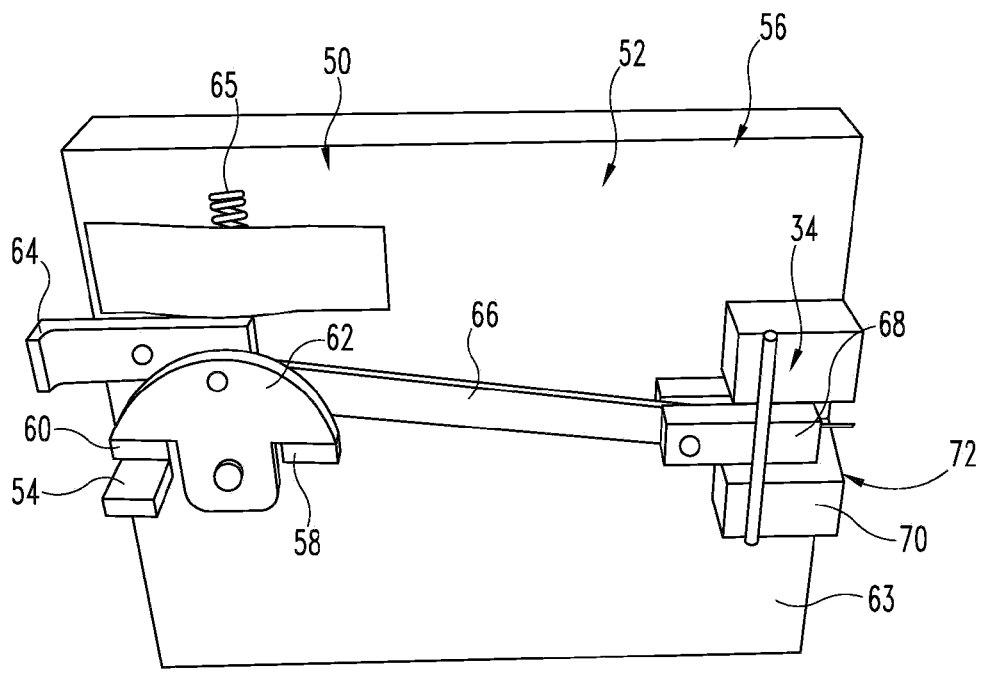
FIG. 3 is a second perspective view of the crank-type lancing mechanism in FIG. 2.

FIGS. 2 and 3 illustrate a lancing device 50 according to another embodiment in which a mechanical structure is used to convert magnetic force to mechanical force for driving the lancet 34. These mechanical structures and/or linkages can also enhance the momentum for the relatively light disposable lancets. The mechanical structure in the illustrated embodiment is a crank mechanism 52 that confines the moving magnets to a circular path. The crank mechanism 52 provides a smooth lancing profile as well as facilitates adjustments to the lancing profile. A drive magnet 54 is attached to a base 56 of the lancing device 50. First 58 and second 60 crank magnets are attached to a crank 62. In the illustrated embodiment, the crank 62 is rotatably mounted to a support structure 63 via a pin, but other structures can be used to facilitate rotation of the crank 62. A trigger 64 that is biased by a spring 65 is used to hold the crank 62 in a cocked position, and the trigger 64 is then used to release the crank 62 in order to fire the lancet 34. A connecting rod 66 is connected between the crank 62 and a lancet carrier 68 to which the lancet 34 is detachably secured. The connecting rod 66 converts the rotary motion of the crank 62 into the reciprocating motion of the lancet 34 that occurs during firing and retraction of the lancet 34. In the embodiment shown, the connecting rod 66 is connected to the crank 62 and the lancet carrier 68 via pins, but other structures, like living hinges, can be used to make the connections. A lancet guide 70 guides the lancet carrier 68 during the firing and retraction motions. The lancet guide 70 has a guide channel 72 in which the lancet carrier 68 is slidably received. The lancet guide 70 guides the lancet 34 during firing and retraction. Like before, FIGS. 2 and 3 show the lancing device 50 without a housing so that the various components can be easily seen, but when in use, the lancing device 50 typically includes a housing as well as other components.

Before firing the lancet 34, common polarity sides of the drive magnet 54 and the first crank magnet 58 are clamped together and held in place with the trigger 64, as is depicted in FIG. 2. This cocking of the lancing device 50 can occur manually by the user turning the crank 62 or in some other manner. Once the trigger 64 is released, the repelling magnetic force between the drive 54 and first crank 58 magnets causes the crank 62 to rotate. The connecting rod 66 converts the rotary motion of the crank 62 into the linear firing motion of the lancet 34 that pierces the tissue. The side of the drive magnet 54 and the side of the second crank magnet 60 that eventually face one another when the lancet 34 is fully retracted have opposite polarities so as to create an attractive force between the two. Once the crank 62 passes the halfway point, the second crank magnet 60 is attracted to the drive magnet 54, which in turn causes the lancet 34 to retract. The crank 62 continues to rotate until the second crank magnet 60 contacts (or comes into close proximity to) the drive magnet 54, as is depicted in FIG. 3. After completing the lancing cycle, the now used lancet 34 can be discarded and replaced with a new one, if so desired. The lancing device 50 can be again cocked for firing in the same fashion described above.

In the above-described lancing device 50, the second crank magnet 60, which is used to retract the lancet 34, remains relatively close to the drive magnet 54 so that the retraction force applied is strong, thereby leading to more consistent lancet retraction velocities, which in turn can lead to reduced pain. Moreover, the mechanical nature of the crank-drive system provides consistent penetration depths. With the drive magnet 54 being stationary during the lancing cycle, the lancing profile also tends to be more consistent because the magnetic fields do not drastically fluctuate. With lancets being generally disposable in nature, there is a tendency to make them smaller and thus lighter. As noted before, the relatively light lancet reduces the resulting piercing energy provided when the lancet pierces the tissue. The increased momentum provided by the heavier crank-type drive system illustrated in FIGS. 2 and 3 enhances the penetrating force of the lancet 34.

Figure 4:
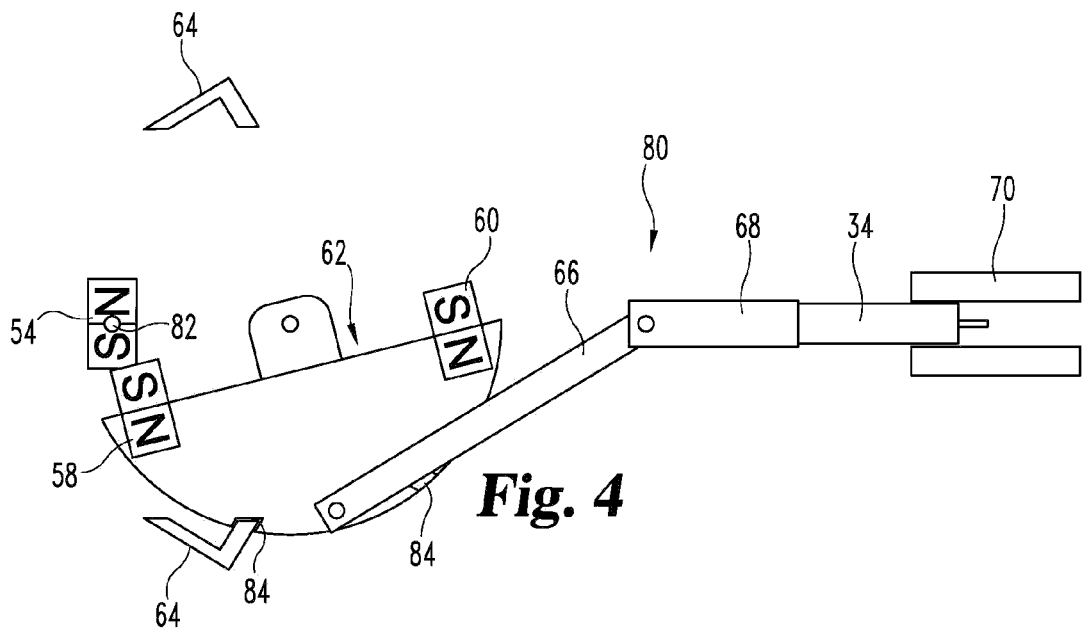
FIG. 4 is a diagrammatic view of a crank-type lancing device according to still yet another embodiment.

A crank-type drive system or lancing device 80 according to another embodiment will now be described with reference to FIGS. 4, 5, 6, and 7. In addition to the advantages found in the system 50 of FIG. 2, the crank-type drive system 80 of FIG. 4 also facilitates contactless cocking in which the user does not have to move the lancet 34 or a plunger to perform cocking. Instead, the user simply changes the polarity between magnets in order to create the potential energy for firing the lancet. This contactless cocking reduces the risk of wear and tear found on traditional plunger mechanisms as well as prevents any plunger jamming during cocking. It further avoids the need for users sticking their fingers inside the lancing mechanism, thereby reducing a potential contamination source. Between tests, the crank-type drive system 80 in FIG. 4 is designed to secure the lancet carrier 68 so as to reduce a source for injury. The lancet carrier 68 is secured at a fixed location so as to avoid any bottoming out issues when the lancet 34 is loaded.

The crank-type drive system 80 in FIG. 4 shares a majority of components in common with the system 50 in FIG. 2. For example, the crank-type drive system 80 includes the lancet 34, the drive magnet 54, the first crank magnet 58, the second crank magnet 60, the crank 62, the trigger 64, the connecting rod 66, the lancet carrier 68, and the lancet guide 70 of the type described above. For the sake of clarity and brevity, these common components will not be again described in great detail, but please refer to the previous discussion. In the illustrated embodiment, the drive magnet 54 is mounted in a moveable manner in order to permit changing of its polarity relative to the crank magnets 58, 60. Specifically, a pivot handle or knob 82 is used to rotate the drive magnet 54. To cock the crank-type drive system 80, the user simply rotates the knob 82 so that the sides of the drive 54 and the crank 58, 60 magnets facing each other have the same polarity. With the drive magnet 54 being moveable, the repulsive magnetic force and resulting firing speed can be adjusted depending on the orientation of the drive magnet 54. For instance, the drive magnet 54 can be oriented so as to not directly face the crank magnets 58, 60 so as to reduce the lancing speed (and/or change the penetration depth). With magnets of common polarity in close proximity to one another, the potential energy for firing the lancet 34 is created. During the lancing cycle, the pivot handle 82 is held in place through frictional resistance so that the drive magnet 54 remains stationary. In comparison to the previous embodiment, the crank-type drive system 80 in the illustrated embodiment has two triggers 64 with corresponding trigger notches 84 on the crank 62 for holding the crank 62 in place at alternating positions, but in other embodiments, a single trigger 64 can be used.

Figure 5:
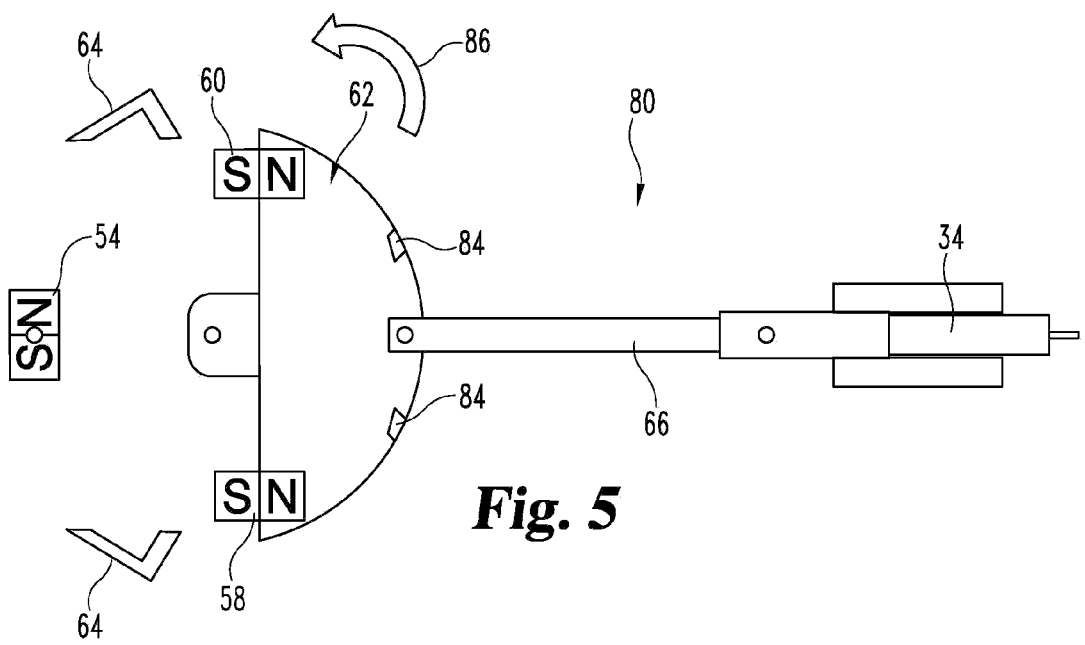
FIG. 5 is a diagrammatic view of the FIG. 4 crank-type lancing device during a lancing cycle.

A technique for operating the crank-type drive system 80 will now be described. Looking at FIG. 4, one of the triggers 64 holds the crank 62 in a cocked state where the facing sides of the drive magnet 54 and the first crank magnet 58 have the same polarity. The end of the crank-type drive system 80 with the lancet 34 is placed against or in close proximity to the tissue to be cut. To fire the lancet 34, the trigger 64 that holds the crank 62 is actuated so as to release the crank 62. The repulsive magnetic force between the drive magnet 54 and the first crank magnet 58 causes the crank 62 to rotate in a counterclockwise direction 86, as is depicted in FIG. 5. The connecting rod converts the rotary motion of the crank 62 into the linear firing motion of the lancet 34. Eventually, the lancet 34 pierces the tissue. The attraction between the facing sides of the drive magnet 54 and the second crank magnet 60, which have opposite polarities, causes the crank 62 to continue to rotate in the counterclockwise direction 86. This in turn causes the lancet 34 to retract from the incision.

Figure 6:
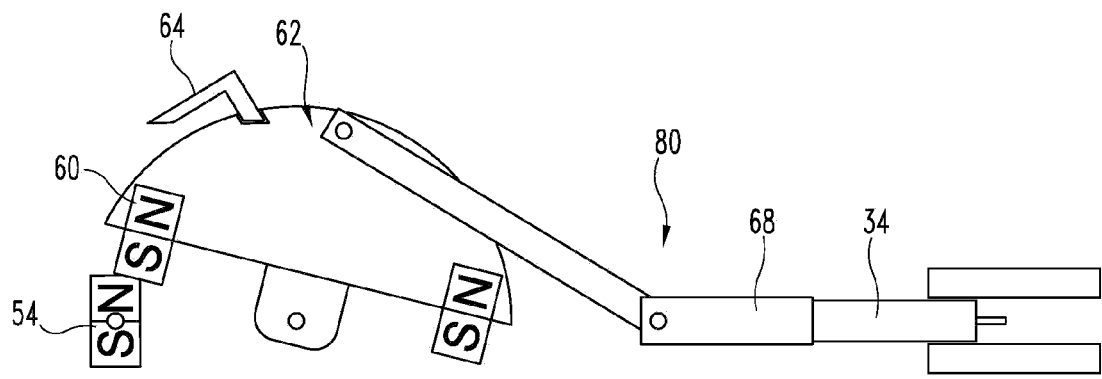
FIG. 6 is a diagrammatic view of the FIG. 4 crank-type lancing device in a fully retracted state.
Figure 6:

Turning to FIG. 6, the crank 62 continues to rotate until the other trigger 64 engages the trigger notch 84 in the crank 62. At this point, the second crank magnet 60 is touching or in close proximity to the drive magnet 54. With the crank 62 locked in place, the user can easily remove and discard the lancet 34, if so desired, without the worry of damage to the crank-type drive system 80 as well as injury. The fixed crank 62 also simplifies loading of the lancet 34 because the user has a fixed target (i.e., the lancet carrier 68) onto which to load the lancet 34. As mentioned before, some traditional spring based systems had the plunger float against the spring such that the lancet carrier moved as the user inserted the lancet. With such a construction, the lancet carrier had a tendency to spring back, which in turn might result in an injury. Having the crank 62 and the lancet carrier 68 locked in place makes loading the lancet 34 onto the lancet carrier 68 safer as well as easier.

Figure 7:
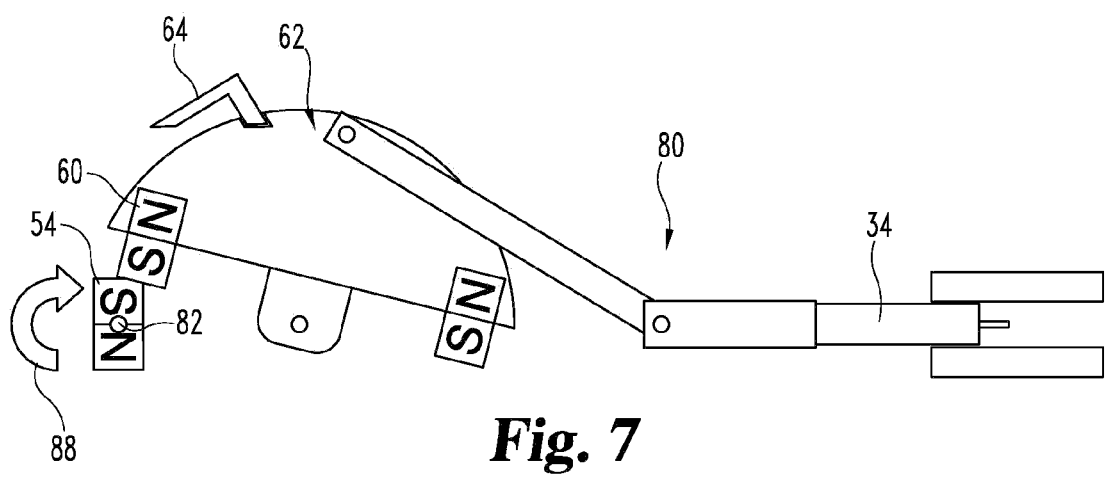
FIG. 7 is a diagrammatic view of the FIG. 4 crank-type lancing device during cocking.
Figure 7:

To cock the crank-type drive system 80, the user rotates the knob 82, as is indicated by arrow 88 in FIG. 7 so that the sides of the drive magnet 54 and the second crank magnet 60 facing each other have the same polarity. In the illustrated embodiment, the drive magnet 54 is held in place through friction. The resulting repulsive force between the drive 54 and second crank magnets 60 creates the potential energy used to fire the lancet 34. Once cocked, the lancet 34 can then be fired in the same fashion described above. To fire the lancet 34, the user actuates the trigger 64, thereby releasing the crank 62. This results in the crank 62 rotating in a clockwise direction. The lancet 34 proceeds to puncture the tissue and is then retracted as the first magnet 58 is attracted to the drive magnet 54. Eventually, the trigger 64 locks the crank 62 in place, and the user is then able to replace the lancet 34 with a new one, if so desired. The user then again can rotate the drive magnet 54 so as to place the crank-type drive system 80 in a cocked state, as is shown in FIG. 4. This process can be repeated for multiple tests.

As noted before, power sources, such as batteries, fuel cells, etc., as well as other components for electromagnetic drive systems tend to fail or are unavailable at the most inappropriate times. A lancing system 90 in FIG. 8 addresses this failure issue by incorporating a permanent magnet drive system similar to those described above to act as a back up in case of failure of the electromagnetic drive. Even when not needed, the permanent magnet drive system can boost the power of the electromagnetic drive for firing and retracting the lancet. In turn, this can reduce the overall size of the electromagnet needed to actuate the lancet, thereby reducing the overall size of the lancing system 90. Moreover, the power assist provided by the permanent magnets can reduce power consumption so as to extend the life of the batteries.

FIGS. 8, 9, 10, 11, and 12 show diagrammatic views of the lancing system 90 during various lancing stages. Looking at FIG. 8, the lancing system 90 shares several components in common with the previously described components, as is indicated by the common reference numerals. For example, the lancing system 90 like before includes the lancet 34, lancet carrier magnet 36, retraction magnet 38, lancet carrier 40, trigger 42, support structure 44, guide channel 46, drive magnet 54, and knob 82. For the sake of clarity as well as brevity, these common features will not be again described in great detail below, but reference is made to the previous discussion of these common features. In the illustrated embodiment, the lancing system 90 includes an electromagnet 92 for firing the lancet 34. The electromagnet 92 is disposed at the end of the guide channel 46 that is opposite the retraction magnet 38.

Figure 8:
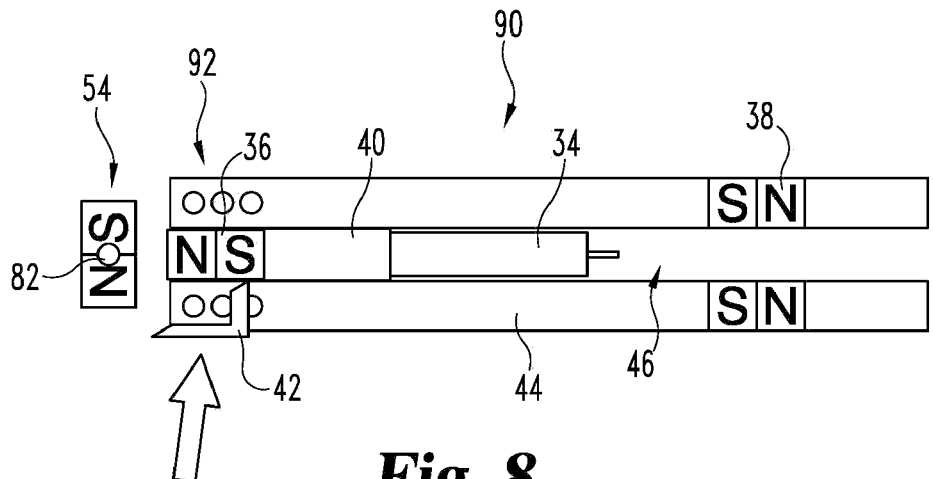
FIG. 8 is a diagrammatic view of a lancing device that includes a permanent magnet and an electromagnet according to a further embodiment.
Figure 9:
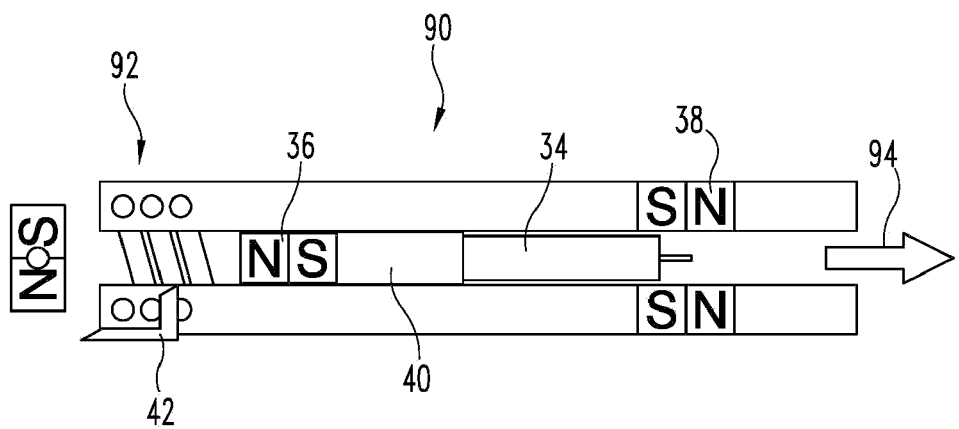
FIG. 9 is a diagrammatic view of the FIG. 8 lancing device when the electromagnet fires a lancet.

When the electromagnet 92 is used, the drive magnet 54 can be positioned or oriented so as to minimize an interference with the operation of the electromagnet 92, as is depicted in FIG. 8. At or before firing of the lancet 34, the electromagnet 92 is energized to generate a magnetic field that repulses the lancet carrier magnet 36. In one embodiment, the user actuates the trigger 42 so as to release the lancet carrier 40 and fire the lancet 34 into the tissue. FIG. 9 shows the lancet 34 being fired towards the tissue, as is indicated by arrow 94. The retraction magnet 38 is oriented so as to repulse the lancet carrier magnet 36. As the lancet carrier 40 travels towards the tissue, the retraction magnet 38 causes the lancet 34 to decelerate, gently stop and reverse direction, thereby retracting the lancet 34 from the tissue.

Figure 10:
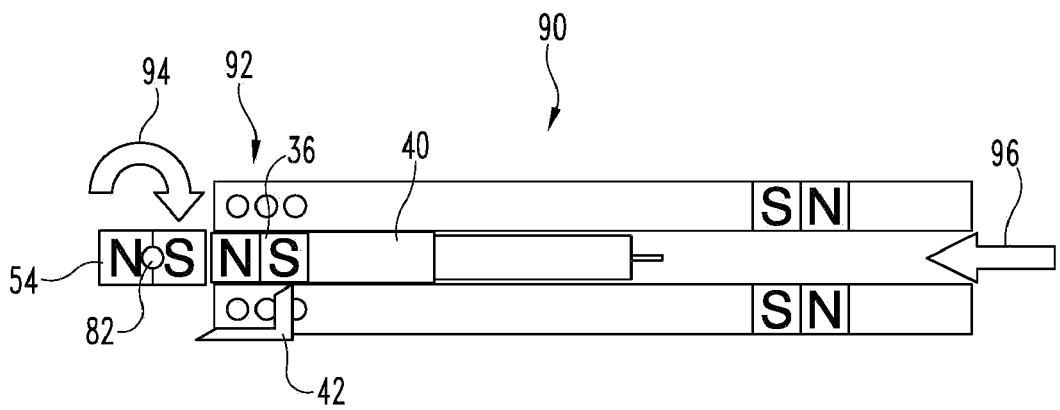
FIG. 10 is a diagrammatic view of the FIG. 8 lancing device when the permanent magnet fully retracts the lancet.
Figure 11:
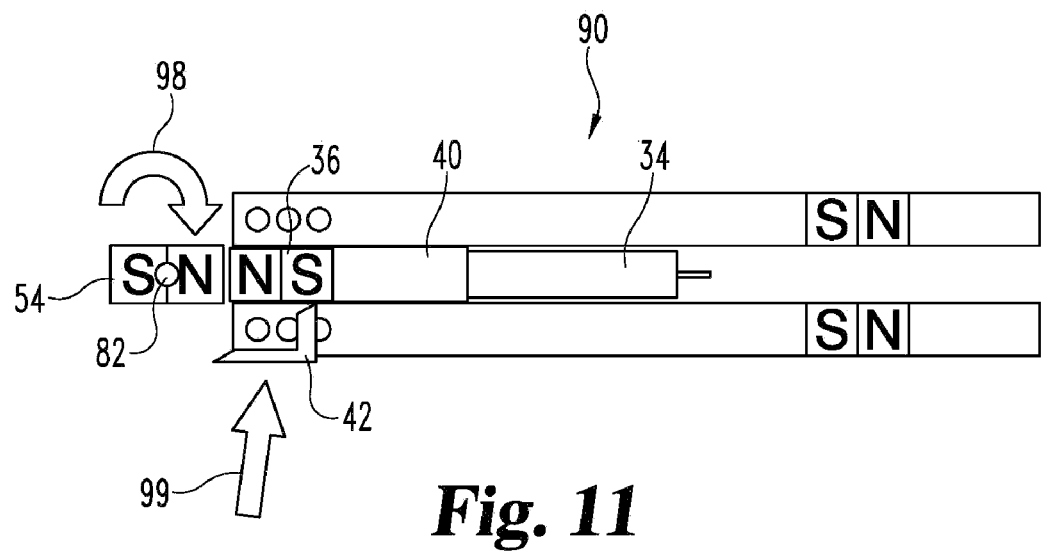
FIG. 11 is a diagrammatic view of the FIG. 8 lancing device when the permanent magnet cocks the lancet.
Figure 12:
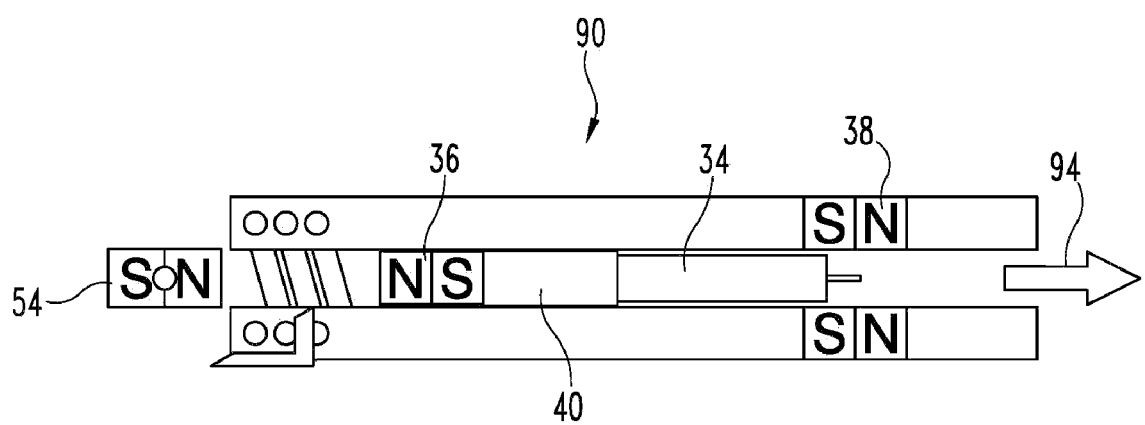
FIG. 12 is a diagrammatic view of the FIG. 8 lancing device when the permanent magnet fires the lancet.

Subsequently, the electromagnet 92 can create a magnetic field to attract the lancet carrier magnet 36 such that the lancet carrier 40 is locked in the fully retracted position by the trigger 42. Considering the retraction magnet 38 retracts the lancet 34 from the tissue, the speed of retraction after removal from the tissue is of little importance such that the lancet carrier 40 can be retracted to the fully retracted position at a relatively slow speed in comparison to when the lancet 34 is within the tissue. To conserve energy, the drive magnet 54 can be used to retract the lancet carrier 40 to the fully retracted position instead of the electromagnet 92, as is shown in FIG. 10. The user rotates the knob 82, as indicated by arrow 94, such that the sides of the drive magnet 54 and the lancet carrier magnet 36 facing each other have opposite polarities. The resulting magnetic attraction between the drive magnet 54 and the lancet carrier magnet 36 cause the lancet carrier 40 to further retract, as depicted by arrow 96, until the lancet carrier 40 is locked by the trigger 42 into the fully retracted position. Afterwards, the drive magnet 54 can be reoriented at the position depicted in FIG. 8 so that the lancing system 90 can be fired again in the same manner as described above.

As mentioned before, the permanent magnet drive system in the lancing system 90 acts as a backup in case of failure or unavailability of the electromagnetic drive. For example, the lancing system 90 can be used even if power is unavailable due to the batteries being drained and/or lack of an external power source. A technique for firing the lancet through this backup system will now be described with reference to FIGS. 11 and 12. As will be appreciated, the lancing system 90 in FIGS. 11 and 12 operates in a fashion similar to what was described above with reference to FIG. 1. To prepare the lancing system 90 for firing, the lancing system 90 is cocked by turning the drive magnet 54 with the knob 82, as is indicated by arrow 98. The drive magnet 54 is oriented such that the sides of the lancet carrier magnet 36 and drive magnet 54 facing each other have the same polarity, which in turn creates a repulsive magnetic force between the two. The drive magnet 54 can be held in place through friction fit or some other holding structure like a ratchet, and the trigger 42 holds the lancet carrier 40 in the now cocked state. To fire the lancet 34, the user actuates the trigger 42 (as indicated by arrow 99) such that the trigger 42 releases the lancet carrier 40. The repulsive magnetic force between the drive magnet 54 and the lancet carrier magnet 36 causes the lancet 34 to move in the firing direction. Eventually, the lancet 34 punctures the tissue. In the illustrated embodiment, the drive magnet is held stationary at least during the firing stroke and when the lancet 34 is within the tissue so that the lancet carrier 40 is driven by a generally consistent magnetic field, thereby avoiding the previously discussed problems associated with fluctuating magnetic fields. Like before, the retraction magnet 38 is oriented so as to repulse the lancet carrier magnet 36. As the lancet carrier 40 travels towards the tissue, the retraction magnet 38 causes the lancet 34 to decelerate, gently stop and reverse direction, thereby retracting the lancet 34 from the tissue. To lock the lancet carrier 40 in the fully retracted position, the drive magnet 54 is oriented in the same manner as described above with reference to FIG. 10 so that the lancet carrier magnet 36 is attracted to the drive magnet 54. Once the lancet carrier 40 is secured in place with the trigger 42, the lancet 34 can be again fired in the same fashion as described above. It should be recognized that between the various lancing cycles, the lancet 34 can be replaced by a new one for hygienic purposes.

Figure 13:
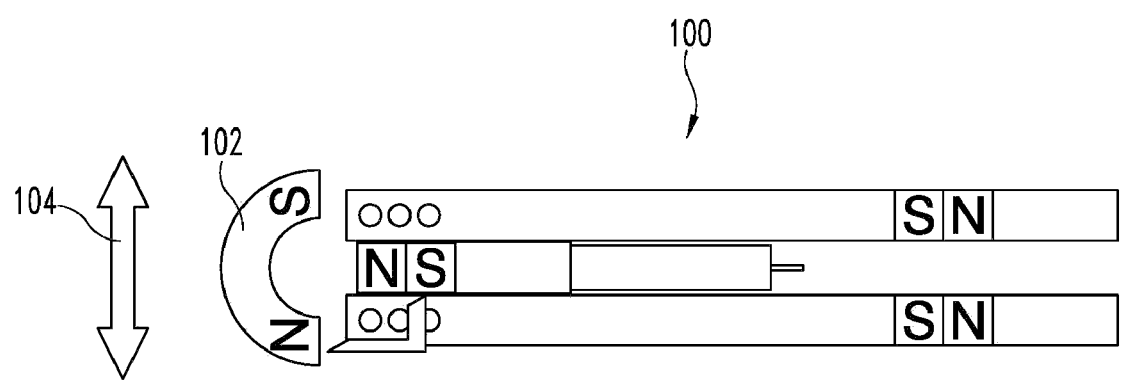
FIG. 13 is a diagrammatic view of a variation of the FIG. 8 lancing device.

FIG. 13 shows a diagrammatic view of a lancing system 100 that is a variation of the lancing system 90 illustrated in FIG. 8. The lancing system 100 in FIG. 13 has the same components and construction as the lancing system 90 in FIG. 8, with the exception that the lancing system 100 has a drive magnet 102 that is shaped differently and moves differently. In particular, the drive magnet 102 in FIG. 13 has a horseshoe shape, and instead of rotationally moving, the poles of the drive magnet 102 are positioned by moving the drive magnet 102 in a linear or sliding fashion, as is indicated by double arrow 104. Like the previous embodiment, the drive magnet 102 is a permanent magnet. The lancing system 100 in FIG. 13 operates in the same fashion as described above with reference to FIGS. 8-12, but the drive magnet 102 is moved linearly instead of being rotated. In some instances where system compactness is a concern, this linear motion of the drive magnet 102 can reduce the overall size of the lancing system 100.

In the illustrated embodiments, the magnets have a general rectangular or horseshoe shape, but the magnets can be shaped differently in other embodiments. For instance, the magnets can be cylindrical or semi-cylindrical in shape. The polarities illustrated in the drawings are used for explanation purposes only, and it should be appreciated that different polarity combinations can be used in other embodiments. For example, in the above description and drawings where the South ends of magnets are facing one another to generate a repulsive force, it should be appreciated that the repulsive force can be generated as well by facing the North ends towards one another. Although the drawings show only a single type of magnet for a system, it should be appreciated that more than one type of magnet can be used. For example, other systems can include more than one drive magnet, lancet carrier magnet, retraction magnet, and/or electromagnet. For example, the crank-type drive systems in other embodiments can include a single crank magnet and two (or more) drive magnets.

It is contemplated that the magnets can move in different paths and in different planes besides the linear or rotary paths illustrated in the drawings and described above. For example, the drive magnet in some of the illustrated embodiments is rotated in order to create a potential difference between the drive and lancet carrier magnets, but in other embodiments, the drive magnet can be slid or moved in a generally linear fashion. Instead of moving the drive magnet, it is contemplated that magnetic shielding can be used to achieve the same effect. Magnetic shielding can also be used elsewhere within the lancing device. Further, it is envisioned that other magnets besides the drive magnet can be moved in order to create the potential difference of cocking the lancing device. For example, the lancet carrier and/or crank magnets can be rotated or otherwise repositioned in order to create a potential difference with the drive magnet that is used to fire and/or retract the lancet.

During lancing and retracting, the drive magnet in the above-described embodiments is held in place through friction, but other structures and/or mechanisms can be used to keep the drive magnet stationary. For example, the drive magnet can be held stationary through a ratchet type mechanism, a clamp type mechanism, a detent type mechanism, etc.

The electromagnet illustrated in the drawings is in the shape of a hollow coil, but it should be recognized that the electromagnet can be configured differently in other embodiments. For instance, the coil can be wrapped around a core and/or the coils can be replaced with different structures. In selected embodiments, the drive magnet can be positioned or oriented to supplement the magnetic field generated by the electromagnet during firing or facilitate retraction of the lancet. In addition, the drive magnet in other embodiments can act like the trigger to hold the lancet in a retracted state by magnetic attraction between the drive magnet and the lancet carrier magnet.

The lancet carrier can also be shaped differently in other embodiments, and the lancet can be secured, permanently or detachably, to the lancet carrier in other manners besides a friction fit. For example, the lancet can be secured using a clamping mechanism, bayonet fit, a screw type connection, via an adhesive, etc., to name just a few examples. The illustrated support and guide structures can take different forms in other embodiments. For instance, guide tubes can be used to guide the lancet during the lancing cycle.

In the above-discussed embodiments, the triggers are generally in the form of a spring-biased L-shaped member that is pivoted to fire the lancet. It should be recognized that the triggers can take different forms in other embodiments. For example, the triggers can be mechanical in nature, electromagnetic in nature, and/or chemical in nature, such as through an adhesive. Moreover, the triggers can be spring biased, biased through some other means, or not biased at all. In the illustrated embodiments, the systems include one or two triggers, but more than two triggers can be used. Moreover, the two-trigger arrangement of FIG. 4 can be replaced by a single trigger. The trigger can engage other components besides the lancet carrier or crank and be located elsewhere in order to maintain the cocked state. For example, the trigger can directly engage the lancet to hold it in place. The trigger in various embodiments can be optional. For example, the trigger in FIG. 8 can be optional such that the energizing of the electromagnet automatically fires the lancet upon being energized.

Although the above-described lancing systems eliminate the need for springs, batteries, and other components, it should be appreciated that other systems with the device can incorporate these components. For example, the device can include a spring biased cover that allows the user to gain access to the device in order to replace lancets or components.

In the illustrated crank-type mechanisms, the crank has a semi-circular shape, but the crank can be shaped differently in other embodiments. The overall crank mechanisms illustrated in the drawings can be configured differently in other embodiments. For example, the pivot pins used to connect the various components in the crank mechanism can be replaced with other types of connectors, like living hinges, screws, etc. The connecting rod can be connected to the crank at different positions than is shown so as to change the stroke and/or timing profile of the lancet.

As used in the specification and claims, the following definitions apply:

The term "lancet" is used in a broader sense and is meant to include any sharp and/or pointed structure for cutting incisions in tissue, such as a needle, blade, knife, scalpel, and the like. The lancet can be, whole or in part, hollow and/or solid. The lancet can be round, flat and/or have other cross-sectional shapes. Further, the lancet can have a single cutting surface or multiple cutting surfaces.

The term "magnet" means any object, material and/or structure having the property of producing a magnetic field external to itself.

The term "permanent magnet" means a type of magnet that generally retains its magnetism after being removed from a magnetic field.

The term "electromagnet" means a type of magnet in which a magnetic field is produced by the flow of an electric current and in which the magnetic field generally disappears when the electric current ceases.

The term "crank" means any device or structure that converts rotary motion to reciprocating motion or vice-versa.

The language used in the claims and specification is to only have its plain and ordinary meaning, except as explicitly defined above. The words in the above definitions are to only have their plain and ordinary meaning. Such plain and ordinary meaning is inclusive of all consistent dictionary definitions from the most recently published Webster's dictionaries and Random House dictionaries.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus, comprising:
    a lancet for forming an incision in tissue;
        a crank being configured to rotate about an axis;
    a connecting rod connecting the lancet to the crank;
    one or more magnets configured to rotate the crank about the axis for actuating the lancet to form the incision;
    the one or more magnets being permanent magnets;
    the one or magnets including
        a first crank magnet attached to the crank,
        a second crank magnet attached to the crank, and
        a drive magnet rotatable relative to the first and second crank magnets;
    a first trigger positioned to hold the crank in a first cocked position where the drive magnet is oriented to create a first repulsive force with the first magnet; and
    a second trigger positioned to hold the crank in a second cocked position where the drive magnet is oriented to create a second repulsive force with the second magnet.

2. The apparatus of claim 1, further comprising:
    means for changing polarities between the drive magnet and the crank magnet.

3. The apparatus of claim 2, further comprising:
    a trigger positioned to hold the crank stationary as the polarities between the crank magnet and the drive magnet are changed to cock the lancet.

4. The apparatus of claim 2, further comprising:
    the means for changing the polarities including at least one of the crank magnet and the drive magnet being moveable to change the polarities between the crank magnet and the drive magnet.

5. The apparatus of claim 4, further comprising:
    the means for changing the polarities including a knob coupled to the drive magnet to rotate the drive magnet.

6. The apparatus of claim 4, further comprising:
the drive magnet being configured to move in a linear fashion.

7. The apparatus of claim 2, further comprising:
the second crank magnet coupled to the crank for facilitating contactless cocking of the lancet.

8. The apparatus of claim 7, further comprising:
both of the crank magnets having ends with the same polarity facing the drive magnet.

9. The apparatus of claim 1, further comprising:
the first trigger positioned to hold the crank in the cocked state where the first crank magnet and the drive magnet are at least in close proximity;
a lancet carrier to which the lancet is secured;
a lancet guide defining a guide channel in which the lancet carrier is disposed; and
the connecting rod connecting the lancet carrier to the crank.

10. The apparatus of claim 1, further comprising:
a lancet carrier to which the lancet is secured;
a lancet guide defining a guide channel in which the lancet carrier is disposed; and
the connecting rod connecting the lancet carrier to the crank.

11. An apparatus, comprising:
a lancet;
a first lancet magnet coupled to the lancet, the first lancet magnet being a permanent magnet, the first lancet magnet being moveable to fire the lancet;
a second lancet magnet;
a drive magnet to move the lancet magnet, the drive magnet being a permanent magnet;
a crank to which the first lancet magnet and the second lancet magnet are secured;
a connecting rod coupling the crank to the lancet;
means for holding the lancet magnet stationary while the polarities of the lancet magnet and the drive magnet facing one another are made the same; and
wherein the means for holding the lancet magnet stationary includes
a first trigger positioned to hold the crank in a first cocked position where the drive magnet is oriented to create a first repulsive force with the first lancet magnet, and
a second trigger positioned to hold the crank in a second cocked position where the drive magnet is oriented to create a second repulsive force with the second lancet magnet.

12. The apparatus of claim 11, further comprising:
the drive magnet being rotatable relative to the first lancet magnet to change the polarities.

13. The apparatus of claim 11, further comprising:
the drive magnet being linearly moveable relative to the first lancet magnet to change the polarities.

14. The apparatus of claim 11, further comprising:
a lancet carrier that couples the lancet to the lancet magnet.

* * * * *